United States Patent [19]

Dahn et al.

[11] Patent Number: 5,531,714
[45] Date of Patent: Jul. 2, 1996

[54] SELF-GUIDING, MULTIFUNCTIONAL VISCERAL CATHETER

[75] Inventors: Michael S. Dahn, Farmington Hills, Mich.; M. Patricia Lange, 32209 Hull, Farmington Hills, Mich. 48336

[73] Assignee: M. Patricia Lange, Farmington Hills, Mich.

[21] Appl. No.: 411,101

[22] Filed: Mar. 27, 1995

Related U.S. Application Data

[63] Continuation-in-part of Ser. No. 332,715, Nov. 1, 1994.

[51] Int. Cl.⁶ .......................... A61M 5/00; A61M 25/00; A61B 5/00
[52] U.S. Cl. ..................... 604/264; 128/634; 128/657; 128/692; 128/772; 604/270
[58] Field of Search .................................. 604/264, 270, 604/280–282; 128/637, 639, 642, 654, 656, 657, 658, 691, 692, 772, 634

[56] References Cited

U.S. PATENT DOCUMENTS

| | | | |
|---|---|---|---|
| 4,822,492 | 11/1989 | Schlanger | 128/637 |
| 4,853,091 | 8/1989 | Mund et al. | 128/637 |
| 4,957,110 | 9/1990 | Vogel et al. | 128/642 |
| 5,184,621 | 2/1993 | Vogel et al. | 128/642 |
| 5,372,133 | 12/1994 | Hogen Esch | 128/642 |

Primary Examiner—C. Fred Rosenbaum
Assistant Examiner—Anh-Tuan T. Nguyen
Attorney, Agent, or Firm—Weiner, Carrier & Burt; Pamela S. Burt; Irving M. Weiner

[57] ABSTRACT

A multifunctional visceral catheter having a self-guiding system in the form of a pair of fiberoptic sensor systems which are sensitive to a predetermined analyte, the analyte being one which is removed from the vascular circuit of interest to a high degree, such as galactose in the hepatic venous system or creatinine in the renal venous system. One of the sensors is disposed on the catheter so as to be positioned within the venous system of interest, while the other sensor remains outside the venous system in the vena cava. A substantial difference between analyte concentration values as measured via the two fiberoptic sensor systems provides immediate confirmation that the catheter is properly positioned. In addition to being self-guiding, the catheter provides for direct sampling of venous blood; includes a fiberoptic system for continuously monitoring oxygen saturation in the hepatic or renal venous blood; and is capable of measuring absolute hepatic or renal blood flow. An integral operating unit incorporates necessary fiberoptic system components such as a light source and signal detector, as well as a microprocessor and program memory for implementing various functions of the catheter.

20 Claims, 3 Drawing Sheets

SELF-GUIDING, MULTIFUNCTIONAL VISCERAL CATHETER

This is a continuation-in-part of application Ser. No. 332,715 filed Nov. 1, 1994.

BACKGROUND OF THE INVENTION

1. Field of the Invention

The present invention relates generally to a multifunctional visceral catheter which is substantially self-guiding, i.e., which may be positioned in a visceral venous system without the need for bedside fluoroscopy or other x-ray devices.

More particularly, the self-guiding system of the catheter according to the invention comprises a fiberoptic sensor system, such as a biochemical substrate optode system, which is sensitive to a predetermined analyte or metabolite. The predetermined analyte has a specific relationship to the organ associated with a given visceral venous system such that values of the analyte within the visceral venous system are substantially different from systemic values of the analyte outside the visceral venous system. In particular, the predetermined analyte may be one having a substantial extraction fraction across the splanchnic bed or vascular circuit being explored. When the catheter according to the invention is properly positioned in the hepatic or renal vein, for example, signals received from the sensor(s) of the fiberoptic system will reflect a sudden, substantial decrease in the given analyte so as to readily confirm proper positioning of the catheter.

The catheter according to the invention is also capable of performing various monitoring and assessment functions. The catheter is capable of continuously monitoring the oxygen saturation in the hepatic or renal venous blood once the catheter is placed in any major hepatic or renal venous vessel. The catheter according to the invention is further capable of measuring absolute hepatic or renal blood flow using a tracer clearance technique. The catheter also permits direct sampling of venous blood, such as hepatic or renal venous blood, for the ex vivo measurement of metabolite concentrations.

2. Description of Relevant Art

Known methods of diagnosing liver and/or kidney dysfunction, as well as assessing various physiological parameters associated with the functioning of these organs, typically require catheterization of the hepatic or renal venous systems. A principal disadvantage associated with known techniques for catheterizing the hepatic and renal venous systems is that bedside fluoroscopy or other x-ray devices are required in order to properly position the catheter. For example, while a thermodilution catheter has been developed for renal blood flow determination which might be applicable to general clinical use, the need for fluoroscopic assistance in positioning such catheter is a critical shortcoming. See M. Brenner, G. L. Schaer, D. L. Mallory, et al, "Detection of renal blood flow abnormalities in septic and critically ill patients using a newly designed indwelling thermodilution renal vein catheter", Chest, Vol. 98, pp. 170–79 (1990).

The present inventors, in their invention disclosed and described in their aforesaid U.S. patent application Ser. No. 332,715 filed Nov. 1, 1994, have overcome the principal shortcoming of known catheterization techniques by providing a self-guiding visceral catheter which can be positioned in either the hepatic or the renal venous systems without the use of bedside fluoroscopy or other x-ray devices. The catheter body preferably comprises a main axial portion with an angled end portion extending therefrom at an acute angle. A sensor disposed on the main axial portion of the catheter is adapted to remain outside the visceral venous system, while a sensor disposed on the angled end portion of the catheter is adapted to be positioned within the visceral venous system. Each of the sensors comprises an electrochemical sensing system including an electrode with a hydratable membrane containing a reagent which detects values of a predetermined analyte. The predetermined analyte is related to the organ associated with the given visceral venous system such that values of the analyte within the visceral venous system are substantially different from systemic values of the analyte outside the visceral venous system. Proper positioning of the catheter within the visceral venous system is readily and immediately confirmed by a large difference in analyte concentrations detected by the two electrochemical sensor systems. Alternatively, a single sensor may be provided on only the angled end portion of the catheter, with proper positioning being confirmed by a substantial decrease in analyte concentration as detected by the single electrochemical sensor system.

Like the visceral catheter of the invention disclosed in U.S. patent application Ser. No. 332,715, the visceral catheter according to the present invention incorporates a self-guiding system which is responsive to the differences in values of a predetermined analyte as measured within the visceral venous system of interest as opposed to outside the visceral venous system so as to confirm correct positioning of the catheter. However, in the visceral catheter according to the present invention, the electrochemical sensor systems are replaced by fiberoptic biochemical sensor systems of various suitable types. Some of the advantages afforded by the use of fiberoptic biochemical sensors include eliminating any direct electrical connection to the patient; avoiding potential electrical interference problems; enhanced detection capabilities; and reduction in size and/or expense of various components.

The visceral catheter according to the invention is multifunctional inasmuch as it also permits continuous monitoring of the oxygen saturation in the hepatic or renal venous blood. In the absence of any known technique for readily assessing individual organ oxygenation, central mixed venous oxygen saturation has commonly been used as an index of global body oxygenation. However, the results of various studies have shown that a marked reduction in hepatic venous oxygen saturation frequently exists in critically ill patients. See, e.g., Michael S. Dahn, M. Patricia Lange, Robert F. Wilson, Lloyd A. Jacobs, and Robert A. Mitchell, "Hepatic blood flow and splanchnic oxygen consumption measurements in clinical sepsis," Surgery, Vol. 107, No. 3, pp. 295–301 (March, 1990). This condition goes undetected when only global body oxygenation is assessed, leaving the physician unaware of a condition which could be therapeutically addressed through the use of cardioactive drugs or blood transfusion. To overcome this problem, the multifunctional visceral catheter according to the present invention is capable of continuously monitoring regional oxygenation. Once the catheter is placed in a major hepatic vessel, hepatic function can be assessed in a more direct fashion than is possible by conventional means, such as by monitoring serum bilirubin or liver enzymes.

The multifunctional catheter according to the invention also permits convenient, direct monitoring of the renal venous system. By positioning the catheter according to the invention in the renal vein, endogenous creatinine clearance and other renal functional indicators can be critically assessed. Further, if inulin and/or para-aminohypurate are available for intravenous infusion, glomerular filtration rate and renal blood flow can be assessed.

SUMMARY OF THE INVENTION

The invention comprises a multifunctional visceral catheter having a catheter body provided with means for guiding the catheter body to a position in which a portion of the catheter body is disposed within a predetermined visceral venous system. The guiding means comprises first and second fiberoptic sensor means for detecting values of a predetermined analyte and for outputting signals related thereto. The first fiberoptic sensor means is disposed on a first portion of the catheter body adapted to remain outside the visceral venous system, while the second fiberoptic sensor means is disposed on a second portion of the catheter body adapted to be positioned within the visceral venous system. The predetermined analyte has a specific relationship to the organ associated with the visceral venous system such that values of the analyte within the visceral venous system are substantially different from systemic values of the analyte outside the visceral venous system. Also included is an integral operating unit comprising detector means, selectively connected to the first and second fiberoptic sensor means, for comparing the signals from the first and second sensor means and for alerting a user to a substantial difference between the signals. The multifunctional catheter further includes third fiberoptic sensor means for monitoring the oxygen saturation of blood in the visceral venous system, the third fiberoptic sensor means being disposed substantially at the distal end of the catheter body. The catheter further includes means for measuring blood flow in the visceral venous system, the blood flow measuring means comprising the first and second fiberoptic sensor means. The integral operating unit further comprises illuminating means for transmitting light to the first, second, and third fiberoptic sensor means; a microprocessor; and program memory programmed for computing concentration values of the predetermined analyte and for storing at least one equation for calculating blood flow values on the basis of the concentration values. The microprocessor receives signals from the first and second fiberoptic sensor means and utilizes the program memory to calculate concentration values of the predetermined analyte based on the signals from the first and second sensor means, and to calculate the blood flow values utilizing the stored equation(s) and the concentration values.

In a preferred embodiment, the catheter body comprises a main axial portion, and an angled distal end portion extending from the main axial portion at an acute angle, such as an angle of substantially 65°. The first and second fiberoptic sensor means each comprises an optode-type sensor which generates fluorescent signals based on detected values of the predetermined analyte.

It is an object of the invention to provide a visceral catheter which may be readily positioned within the hepatic or renal venous system by virtue of a novel self-guiding sensor arrangement which utilizes the difference in concentration of a given analyte within the visceral venous system, as opposed to outside that venous system, to readily confirm proper positioning of the catheter. To this end, the catheter may alternatively include a single fiberoptic sensor system provided only at the distal end portion of the catheter, such that a substantial decrease in detected analyte values will alert the user to proper positioning of the distal end portion within the visceral venous system.

The above and further objects, details and advantages of the invention will become apparent from the following detailed description, when read in conjunction with the accompanying drawings.

DETAILED DESCRIPTION OF PREFERRED EMBODIMENTS

Figure 1:
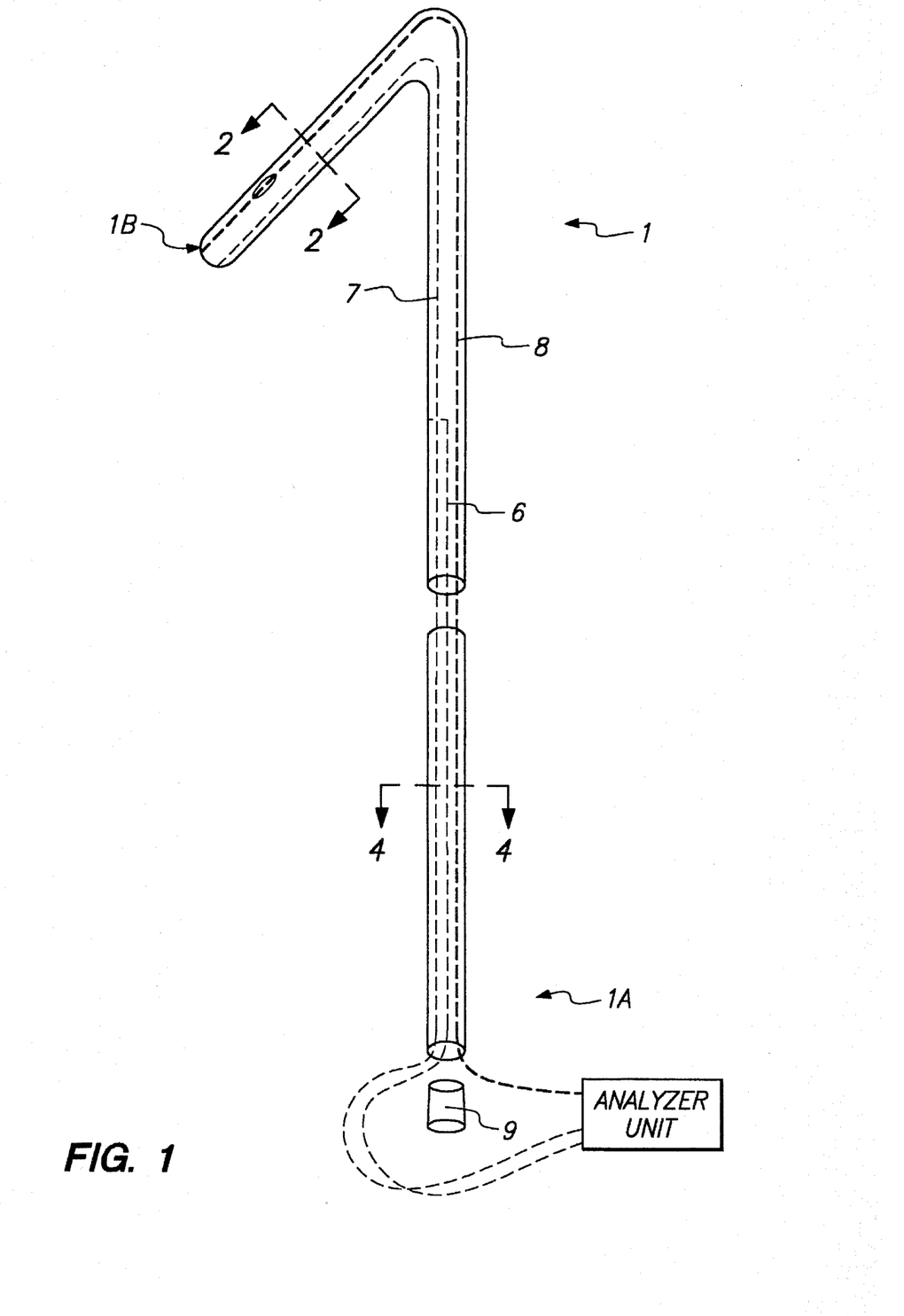
FIG. 1 depicts a schematic perspective view of a preferred embodiment of the multifunctional visceral catheter according to the invention.

With reference to FIG. 1, the self-guiding, multifunctional visceral catheter 1 according to a first preferred embodiment of the invention comprises a main catheter body having a proximal end 1A and a distal end 1B. The catheter 1 may comprise, for example, a 7F polyvinyl chloride diagnostic catheter which is designed for passage through an introducer system via the transfemoral venous route. It is contemplated, however, that other suitable catheters may alternatively be employed.

The distal end portion of catheter 1 is bent at an acute angle to facilitate spontaneous engagement of the distal end of the catheter with a desired vein during positioning, as described below. In the preferred embodiment, the portion of catheter 1 including distal end 1B is disposed at an angle of substantially 65° relative to the main axial portion of the catheter which includes proximal end 1A. It will be understood, however, that the angle may be varied as necessary depending upon the particular application.

Figure 2:
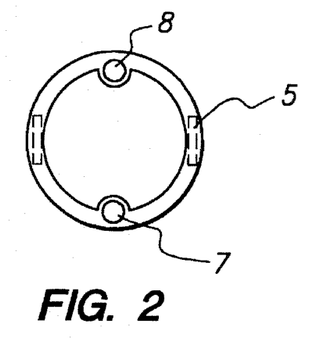
FIG. 2 is a cross-sectional view taken along line 2—2 in FIG. 1.
Figure 3:
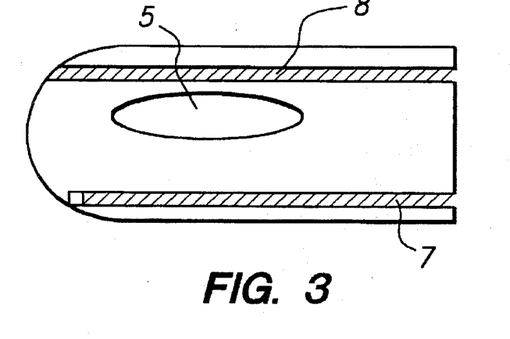
FIG. 3 is a cut-away view of the distal end of the catheter shown in FIG. 1.

With reference to FIGS. 1–3, catheter 1 is substantially hollow along its length, with the distal end portion provided with side vents 5 for blood aspiration. Extending along the inside surface of catheter 1 are optical fibers 6 and 7 which are preferably retained in position along the inside surface of catheter 1 by being embedded within the polyvinyl chloride or other material from which catheter 1 is fabricated. Optical fibers 6 and 7 each form part of respective fiberoptic biochemical sensor systems in accordance with the invention, as will be described in detail below.

Also provided within catheter 1, and extending along the entire length from proximal end 1A to distal end 1B, is an optical fiber 8. Preferably, optical fiber 8 is retained in position along the inside surface of catheter i in the same manner as optical fibers 6 and 7, i.e., by being embedded within the polyvinyl chloride or other material from which catheter 1 is fabricated. Optical fiber 8 is used for monitoring oxygen saturation, as will be described below.

Figure 4:
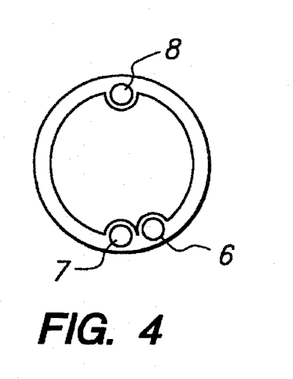
FIG. 4 is a cross-sectional view taken along line 4—4 of FIG. 1.
Figure 5:
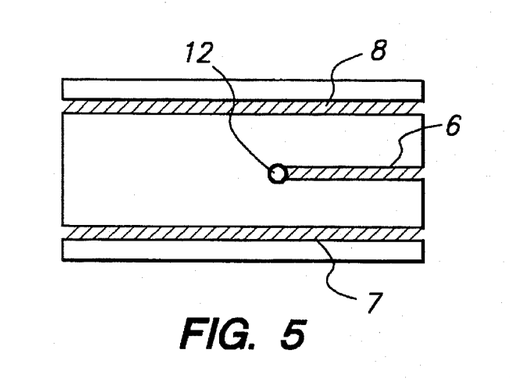
FIG. 5 is a cut-away view of a portion of the catheter shown in FIG. 1, depicting various parts of the fiberoptic systems of the catheter.

As shown in FIG. 4, the optical fibers 6 and 7 may desirably, but not necessarily, be positioned substantially next to each other so as to extend along an inside surface portion of catheter 1 which is substantially opposite optical fiber 8. With reference to FIGS. 1–5, optical fiber 6 extends from proximal end 1A of catheter 1 to a fiberoptic biochemical sensor 12 disposed on the main axial portion of catheter 1 (e.g., substantially 15 cm from the distal tip of the catheter), while optical fiber 7 extends from proximal end 1A to a fiberoptic biochemical sensor 14 disposed on the angled distal end portion of the catheter. The proximal ends of optical fibers 6 and 7 are adapted to be connected with an Analyzer Unit as shown in FIG. 1 and as described in detail below. Also provided at proximal end 1A of catheter 1 is a catheter hub 9.

Figures 6, 7:
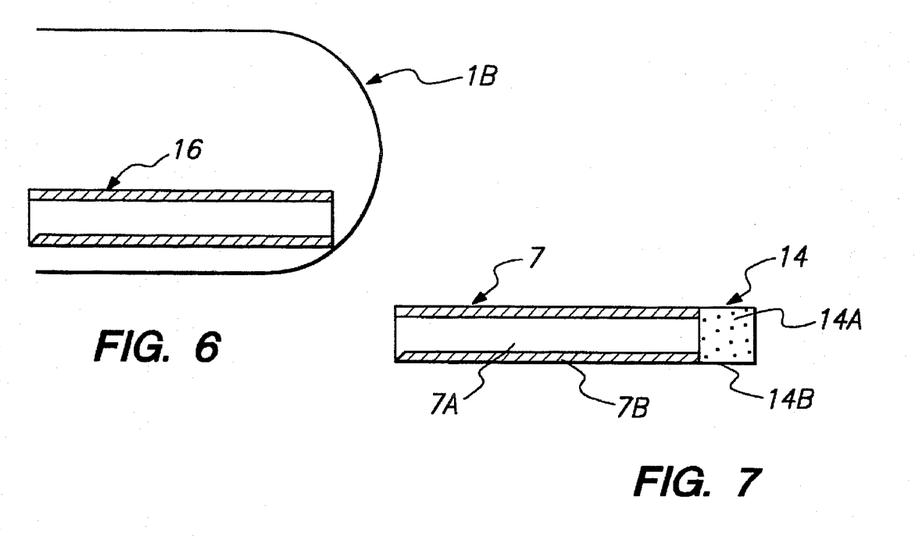
FIG. 6 is an exploded view of the catheter tip depicting an optical fiber of a fiberoptic system of an alternative embodiment of the catheter.
FIG. 7 shows an optical fiber and optode-type sensor of a fiberoptic system employed in the catheter according to the preferred embodiment of the invention.

The two fiberoptic biochemical sensor systems in accordance with the invention comprise the optical fiber 6 and biochemical sensor 12 on the one hand, and the optical fiber 7 and biochemical sensor 14 on the other, together with the Analyzer Unit with which optical fibers 6 and 7 are connected. In a preferred embodiment, the two sensor systems each comprise a substrate optode such as shown in FIG. 7. Although only optical fiber 7 and sensor 14 of the distal sensor system are shown in FIG. 7, it will be understood that the proximal sensor system including optical fiber 6 and sensor 12 is of substantially the same construction.

For a general discussion of fiberoptic sensors used in medical applications, see, for example, J. S. Schultz, "Medical Applications of Fiberoptic Sensors", Medical Instrumentation, Vol. 19, pp. 158–63 (1985). For a discussion of the characteristics of substrate optode systems see, for example, N. Uwira, N. Opitz and D. W. Lubbers, "Influence of enzyme concentration and thickness of the enzyme layer on the calibration curve of the continuously measuring glucose optode", Adv. Exp. Med. Biol., Vol. 169, pp. 913–21 (1984); and K. P. Volkl, N. Opitz, and D. W. Lubbers, "Temperature dependence of enzyme optodes as exemplified by the glucose optode", Adv. Exp. Med. Biol., Vol. 222, pp. 199–204 (1984).

Figure 8:
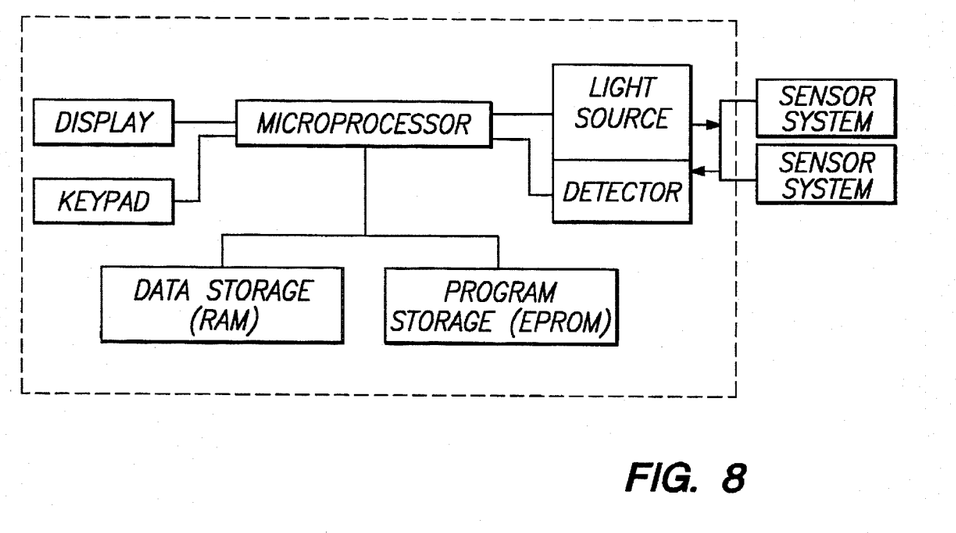
FIG. 8 depicts a box diagram of an Analyzer Unit for operating all the multifunctional elements of the catheter according to the invention.

As shown in FIG. 7, the optical fiber 7 is comprised of a core 7A surrounded by a suitable sheath or clad 7B. Provided at the distal end of optical fiber 7 is the biochemical sensor 14 comprised of biochemical sensor material 14A encased within a semipermeable membrane 14B. In a preferred embodiment, the membrane 14B may comprise a Cuperphan membrane (Cuperphan, Enkar, Germany). While the biochemical sensor material 14A may take various forms, where the catheter is to be positioned in the hepatic venous system the sensor is adapted to detect analytes specific to the liver, such as plasma galactose. In a preferred embodiment, galactose oxidase and luminol are applied to the optical fiber tip within the Cuperphan membrane. Galactose is freely diffusible into the tip via the Cuperphan membrane. When galactose is detected in the plasma, the galactose oxidase in the sensor material liberates hydrogen peroxide which then reacts with luminol to generate fluorescence according to the following scheme:

The Analyzer Unit to which the proximal ends of optical fibers 6 and 7 are connected comprises all necessary fiberoptic system components such as at least one light source, detection means, a microprocessor, and the like, as shown in FIG. 8. The light source transmits excitation light through optical fibers 6, 7 to excite fluorescence of the optodes. The returning fluorescent signals, which vary with the relative concentration of galactose (or other plasma substrate), are received by the detector and are measured and compared with each other. The user is then alerted to a substantial difference in the respective fluorescent signals received from sensors 12 and 14 by means of a visual display and/or an audio signal.

Use of catheter 1 as a hepatic catheter will now be described with reference to FIGS. 1–7. As an initial procedure, an intravenous galactose infusion is initiated in a patient. This may entail, for example, the infusion of a priming bolus (e.g., 50 to 100 ml) of 5% to 7% galactose, followed by a continuous infusion at 100 ml/hour until a steady-state galactose concentration is reached. Once the intravenous galactose infusion has been initiated, the catheter 1 may be advanced transfemorally through the venous system. As the distal tip 1B reaches the hepatic venous system, it will spontaneously engage the major hepatic veins, i.e., it will spontaneously advance into the hepatic vein when the tip is in proximity thereto. Thus, the distal sensor 14 will be disposed within the hepatic venous system, while the proximal sensor 12 will remain in a vessel outside the hepatic venous system, i.e., in the inferior vena cava in the operable position of catheter 1.

It is known that the extraction fraction of galactose across the splanchnic bed is greater than 90% in normal control subjects and 75% in critically ill septic patients. See Michael S. Dahn, M. Patricia Lange, Robert F. Wilson, Lloyd A. Jacobs, and Robert A. Mitchell, "Hepatic blood flow and splanchnic oxygen consumption measurements in clinical sepsis," Surgery, Vol. 107, pp. 295–301 (1990). This large gradient of galactose will be readily detected by a comparison of the fluorescent signals from the two sensor 12 and 14. The hepatic venous sensor, i.e., the distal sensor 14, will detect a low concentration of galactose compared to that detected by proximal sensor 12 which remains in the inferior vena cava and thus measures systemic, or pre-hepatic galactose levels.

From the foregoing it will be understood that the self-guiding system of catheter 1 permits positioning of the catheter in the hepatic venous system without any need for bedside fluoroscopy or other x-ray devices. By virtue of the shape of catheter 1, the angled distal end 1B thereof will spontaneously advance into the hepatic vein when the tip is in proximity thereto. This positioning of the catheter within the hepatic vein is then readily and immediately confirmed by the large difference in galactose concentrations as reflected by the fluorescent signals received from the two fiberoptic sensor systems.

In an alternative hepatic catheter construction according to the invention, the biochemical sensor material of sensors 12 and 14 may comprise galactose oxidase mixed with an alternative fluorescent agent, such as pyrene butyric acid. In a manner similar to that described above, galactose detected in the blood compartment reacts with the galactose oxidase to produce hydrogen peroxide. The biochemical sensor material in the optode tip also includes catalase, which converts hydrogen peroxide to oxygen. The oxygen in turn quenches the fluorescence emitted by the pyrene butyric acid, thereby serving as a detection mechanism. The scheme is as follows:

O₂ quenches pyrene butyric acid fluorescence

In this alternative embodiment then, the degree of fluorescence quenching is dependent upon the concentration of galactose detected in either the vena cava or the hepatic vein. A comparison of the returning fluorescent signals from sensors 12 and 14 will thus permit ready positioning of the catheter tip within the hepatic vein in substantially the same manner as described above.

With the dual sensor embodiments of the invention as described above, because distal sensor 14 is ultimately positioned in the hepatic venous system while proximal sensor 12 remains in the vena cava, simultaneous monitoring of the vena cava and hepatic venous analyte concentration gradient is attained, which may be used in determining liver blood flow measurement. Notwithstanding, the invention also contemplates that the catheter 1 may alternatively be provided with only a single sensor system 7, 14 on the angled distal end portion of the catheter, while the sensor system 6, 12 on the main axial portion of the catheter is eliminated. In such a modification, only the concentration of the predetermined analyte (e.g., galactose) within the visceral venous system of interest will be sensed, and correct positioning of the distal end of catheter 1 will be confirmed on the basis of a substantial decrease in the predetermined analyte as detected by the single sensor. In other words, when the distal end of catheter 1 enters the visceral venous system, the signals sent by sensor system 7, 14 will reflect a sudden, substantial decrease in the given analyte. The user would be alerted to the sudden decrease in analyte concentration by means of a visual and/or audio signal.

The invention further contemplates the use of a simplified fiberoptic system to measure light at the catheter tip at a predetermined wavelength, such as shown in FIG. 6. An optical fiber 16 may take the form of a fiberoptic filament bundle extending from the proximal end 1A of catheter 1 to the distal tip 1B thereof, and having a core diameter of substantially 100 μm. The optical fiber 16 forms part of a simple reflectance spectrophotometric system, with a portion of the fibers in the filament bundle functioning as light transmission elements and the remaining fibers functioning as receiving elements for reflected and refracted light. The predetermined wavelength is selected to coincide with the absorption or fluorescence characteristics of an analyte which is selectively cleared from the blood by the liver. By way of example, it is known that indocyanine green ("ICG") dye is selectively extracted by the liver. By transmitting light along optical fiber 16 at a wavelength of 805 nanometers, which is the peak absorbance of ICG dye and the isosbestic point of hemoglobin, the reflection of differing intensities of light will correspond to the relative concentration of ICG dye in the vena cava as opposed to that in the hepatic venous system. As in the foregoing embodiments, once the distal end of catheter 1 is advanced from the vena cava into the hepatic venous system, the fiberoptic system will measure a sudden change in fluorescence or absorbance intensity to which the user may be alerted by an audio and/or visual signal.

Where the catheter 1 is to be positioned in the renal venous system, the construction of catheter 1 is substantially the same as described above except that the fiberoptic biochemical sensor(s) are adapted to be sensitive to a predetermined analyte or metabolite which is specific to the kidney, such as creatinine. By way of example, the sensor(s) may be formed with suitable biochemical sensor materials so as to generate fluorescence in reaction to the diffusion of creatinine into the sensor tip. The creatinine sensing fiberoptic system will detect a large difference between the creatinine concentration in the renal vein (sensor system 7, 14) and systemic creatinine concentration in the inferior vena cava (sensor system 6, 12). It is known, for example, that substantially 90% of creatinine is extracted across the renovascular circuit. The creatinine concentration detected by sensor system 7, 14 will thus be much lower than that detected by sensor system 6, 12 in the inferior vena cava.

The biochemical sensor material to be employed in such an optode-type sensor which is sensitive to creatinine may be adapted from known membrane bound electrode systems in which hydrogen peroxide is liberated, as in the following scheme:

The liberated hydrogen peroxide then reacts with a suitable fluorescent agent incorporated in the biochemical sensor material to generate fluorescence in a manner similar to the galactose-sensitive optode described in detail above.

As with the single-sensor embodiment of the hepatic catheter described above, the renal catheter may comprise only the sensor system 7, 14 on the angled distal end portion of the catheter. When the distal end of catheter 1 enters the renal vein, the signals sent by sensor system 7, 14 will reflect a sudden, substantial decrease in the predetermined analyte, such as creatinine. The user would be alerted to the sudden decrease in analyte concentration by means of a visual and/or audio signal.

While the fiberoptic sensor systems of the invention have been described as being sensitive to either galactose for liver applications, or creatinine for kidney applications, it will be understood that the sensor systems provided on catheter 1 are not limited to these particular analytes. It is contemplated that the sensor systems may alternatively be adapted to be sensitive to other analytes or metabolites having a significant extraction fraction across the splanchnic bed, renovascular circuit, or other vascular circuit to be explored.

The catheter 1 as described above, in addition to being self-guiding, is capable of performing a number of assessment and monitoring functions. Once the catheter 1 is positioned in the hepatic or renal venous system, direct samples of hepatic or renal venous blood may be taken via catheter 1 for the ex vivo measurement of metabolite concentrations. The catheter 1 is also capable of measuring absolute hepatic or renal blood flow using a tracer clearance technique. For example, if a known infusion rate of galactose is provided (e.g., 100 ml/hour), the data from the fiberoptic sensor systems can be used to calculate hepatic blood flow using a galactose clearance technique, such as described in the aforesaid publication by Dahn et al which is incorporated herein by reference thereto. To this end, the Analyzer Unit shown in detail in FIG. 8 includes program storage memory for storing one or more equations which permits the microprocessor to calculate galactose concentration values on the basis of signals received from the fiberoptic sensor systems, with data being stored in data storage memory and retrievable by the user via a display.

Data inputs to be made by the user, such as the galactose infusion rate, may be made via a keypad.

By way of example, the following equation can be used to measure hepatic blood flow ("HBF"):

$$HBF = \frac{\text{Galactose infusion rate}}{SS(EF)}$$

where SS is the net steady-state blood galactose concentration, and EF is the extraction fraction for galactose across the splanchnic bed.

Similarly, the intravenous infusion of inulin and/or para-aminohypurate permits the assessment of glomerular filtration rate and renal blood flow with catheter 1.

In addition, once catheter 1 is positioned in any major hepatic or renal venous vessel, the oxygen saturation in the hepatic or renal venous blood can be continuously monitored via a fiberoptic system comprising optical fiber 8. The optical fiber 8 may comprise a fiberoptic filament bundle forming part of a commercially-available simple reflectance spectrophotometric system, such as, for example, the system sold under the trademark "OPTICATH" by Oximetrix, Inc. of Mountain View, Calif. In such system, a portion of the filaments in the optical fiber function as fiberoptic transmission elements, while the remaining filaments function as receiving elements for reflected and refracted light. The differential wavelength absorption characteristics of hemoglobin in the oxygenated vs. deoxygenated state permit assessment of blood oxygenation based upon light reflected into the receiving filaments. The relative proportion of oxygenated vs. deoxygenated reflected light is electronically processed by the Analyzer Unit to interpret the fraction of oxygen saturation of the hemoglobin in vivo. See John M. Sperinde and Kathi M. Senelly, "The Oximetrix® Opticath® Oximetry System: Theory and Development", Technical Bulletin, Oximetrix, Inc., Mountain View, Calif.

Alternatively, the fiberoptic system comprising optical fiber 8 may be of the type available from Puritan-Bennett Corporation of Carlsbad, Calif. (Model PB3300 Intra-Arterial Blood Gas Monitoring System). In such system, the fiberoptic element is coated with a fluorescent dye at the distal end portion. The fluorescence intensity of the dye is related to the ambient oxygen concentration at the catheter tip, so that the reflected fluorescence intensity can be electronically interpreted by processing means in the Analyzer Unit to estimate in vivo oxygen concentration. See Terry Lumsden, William R. Marshall, George A. Divers and Samuel D. Riccitelli, "The PB 3300 intraarterial blood gas monitoring system", Journal of Clinical Monitoring, Vol. 10, pp. 59-66 (1994).

It will be understood, however, that the fiberoptic system for monitoring oxygen saturation as employed in catheter 1 is not limited to the foregoing specific systems, and that any suitable fiberoptic system may alternatively be employed. For example, the optical fiber 8 may be replaced by an oxygen optode sensor system having structural and functional features similar to the optode-type sensors systems 6, 12 and 7, 14 described above, thus affording the advantage of a common technology for the entire optical system of the catheter. It is further contemplated that the catheter 1 according to the invention may be provided without the optical fiber 8, if desired, so as to provide a self-guiding visceral catheter having all of the above-discussed capabilities except oxygen saturation monitoring.

The invention contemplates that the Analyzer Unit shown in FIG. 8 serves as a single common operating unit for all the various components of catheter 1, regardless of which of the various types of fiberoptic sensors described above are actually used in constructing the catheter. In this respect, it will be understood that the Analyzer Unit integrally comprises, preferably in a single compact case, all necessary operating system components including fiberoptic light source(s); fiberoptic signal detector(s); fiberoptic lenses, mirrors, and/or filters, if necessary; a microprocessor with associated data storage and program storage memory; a keypad for user input; a visual display; audio alarm means; and/or any other required components for operating the various multifunctional elements of catheter 1. The microprocessor and program storage memory preferably function as a centralized information processing unit for operation of the various elements of the catheter.

While there have been described above what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

We claim:

1. A visceral catheter, comprising:

a catheter body;

sensor means for detecting values of a predetermined analyte both within and outside a predetermined visceral venous system and for outputting signals related thereto, said sensor means being disposed on a portion of said main catheter body which, in an operable position of said catheter, is positioned within said predetermined visceral venous system;

said sensor means being selectively connected to detector means for receiving and processing signals from said sensor means;

said predetermined analyte having a specific relationship to an organ associated with said predetermined visceral venous system such that values of said analyte within said visceral venous system are substantially lower than systemic values of said analyte outside said visceral venous system;

said sensor means comprising a fiberoptic sensor system; and said detector means processes said signals from said fiberoptic sensor system and alerts a user to a substantial decrease in said values of said analyte when said sensor means is disposed within said predetermined venous system in said operable position of said catheter.

2. A visceral catheter according to claim 1, wherein:

said catheter body comprises a main axial portion including a proximal end of said catheter body, and an angled distal end portion extending from said main axial portion at an angle;

said portion of said catheter body which is positioned within said predetermined venous system in said operable position of said catheter comprises said angled distal end portion of said catheter body;

said fiberoptic sensor system comprises:

an optical fiber extending along said catheter body from said proximal end thereof to said angled distal end portion of said catheter body; and a light source operatively cooperating with a proximal end portion of said optical fiber so as to transmit light to said optical fiber.

3. A visceral catheter according to claim 2, wherein:

said predetermined visceral venous system comprises the hepatic venous system;

said predetermined analyte comprises galactose;

said fiberoptic sensor system further comprises an optode provided at a distal end of said optical fiber, said optode comprising biochemical sensor material provided within a semipermeable membrane; and said biochemical sensor material generates fluorescent signals which vary according to detected values of galactose.

4. A visceral catheter according to claim 3, wherein:

said biochemical sensor material comprises galactose oxidase and luminol.

5. A visceral catheter according to claim 3, wherein:

said biochemical sensor material comprises galactose oxidase, pyrene butyric acid, and catalase.

6. A visceral catheter according to claim 2, wherein:

said optical fiber forms part of a simple reflectance spectrophotometric system; and said light source transmits light to said optical fiber at a predetermined wavelength which corresponds to absorption characteristics of said predetermined analyte.

7. A visceral catheter, comprising:

a catheter body having a proximal end and a distal end;

means for guiding said catheter body to an operable position in which a portion of said catheter body is disposed within a predetermined visceral venous system, said guiding means comprising:

first fiberoptic sensor means for detecting values of a predetermined analyte in a vessel disposed outside said visceral venous system and for outputting signals related thereto, said first fiberoptic sensor means being disposed on a first portion of said catheter body which, in said operable position of said catheter body, remains outside said visceral venous system;

second fiberoptic sensor means for detecting values of said predetermined analyte within said visceral venous system and for outputting signals related thereto, said second fiberoptic sensor means being disposed on a second portion of said catheter body which, in said operable position of said catheter body, is positioned within said visceral venous system;

said catheter body comprising a main axial portion extending from said proximal end and an angled distal end portion extending from said main axial portion, said second portion of said catheter body being disposed on said angled distal end portion of said catheter body;

said predetermined analyte having a specific relationship to an organ associated with said predetermined visceral venous system such that values of said analyte within said visceral venous system are substantially different from systemic values of said analyte outside said visceral venous system;

said first and second fiberoptic sensor means being selectively connected to detector means for comparing said signals from said first and second fiberoptic sensor means and for alerting a user to a substantial difference between said signals;

each of said fiberoptic sensor means including an optical fiber having a light-receiving end portion; and illuminating means for transmitting light to said light-receiving end portions of each of said optical fibers.

8. A visceral catheter according to claim 7, wherein:

said catheter body comprises a main axial portion including said proximal end and an angled distal end portion extending from said main axial portion at an acute angle;

said first portion of said catheter body is disposed on said main axial portion of said catheter body, and said second portion of said catheter body is disposed on said angled distal end portion of said catheter body;

said optical fiber of said first fiberoptic sensor means extends along said catheter body from said proximal end thereof to a part of said main axial portion of said catheter body; and said optical fiber of said second fiberoptic sensor means extends along said catheter body from said proximal end thereof to said angled distal end portion of said catheter body.

9. A visceral catheter according to claim 8, wherein:

said first fiberoptic sensor means further comprises an optode provided at an end of said optical fiber disposed at said part of said main axial portion;

said second fiberoptic sensor means further comprises an optode provided at a distal end of said optical fiber;

each of said optodes comprises biochemical sensor material provided within a semipermeable membrane;

said predetermined visceral venous system comprises the hepatic venous system;

said predetermined analyte comprises galactose; and said biochemical sensor material is generates fluorescent signals which vary according to detected values of galactose.

10. A visceral catheter according to claim 9, wherein:

said biochemical sensor material comprises galactose oxidase and luminol.

11. A visceral catheter according to claim 9, wherein:

said biochemical sensor material comprises galactose oxidase, pyrene butyric acid, and catalase.

12. A visceral catheter according to claim 8, wherein:

each said optical fiber forms part of a simple reflectance spectrophotometric system; and said illuminating means transmits light to said optical fibers at a predetermined wavelength which corresponds to absorption characteristics of said predetermined analyte.

13. A visceral catheter according to claim 7, wherein:

said catheter body is substantially hollow; and each said optical fiber is embedded in an inner surface of said catheter body.

14. A visceral catheter according to claim 7, wherein:

said catheter further comprises means for monitoring the oxygen saturation of blood in said visceral venous system;

said oxygen saturation monitoring means comprises an optical fiber extending along said catheter substantially from said proximal end to said distal end of said catheter body.

15. A visceral catheter according to claim 14, wherein:

said oxygen saturation monitoring means comprises a simple reflectance spectrophotometric system.

16. A visceral catheter according to claim 14, wherein:

said oxygen saturation monitoring means further comprises an oxygen optode provided at a distal end of said optical fiber of said monitoring means.

17. A visceral catheter according to claim 7, further comprising:

means for measuring blood flow in said visceral venous system, said blood flow measuring means comprising said first and second fiberoptic sensor means;

an integral operating unit for operating said first and second fiberoptic sensor means and said blood flow measuring means, said integral operating unit comprising said detector means and said illumination means;

said integral operating unit further comprising a microprocessor and program memory, wherein:

said program memory is programmed for computing concentration values of said predetermined analyte, and stores at least one equation for calculating blood flow values based on said concentration values; and said microprocessor receives said signals from said first and second fiberoptic sensor means and utilizes said program memory to calculate concentration values of said predetermined analyte based on said signals from said first and second fiberoptic sensor means, and to calculate said blood flow values utilizing said at least one stored equation and said concentration values.

18. A multifunctional visceral catheter, comprising:

a catheter body;

means for guiding said catheter body to an operable position in which a portion of said catheter body is disposed within a predetermined visceral venous system;

said guiding means comprising first fiberoptic sensor means for detecting values of a predetermined analyte in a vessel disposed outside said visceral venous system and for outputting signals related thereto, and second fiberoptic sensor means for detecting values of said predetermined analyte within said visceral venous system;

said first fiberoptic sensor means being disposed on a first portion of said catheter body which, in said operable position of said catheter body, remains outside said visceral venous system, and said second fiberoptic sensor means being disposed on a second portion of said catheter body which, in said operable position of said catheter body, is positioned within said visceral venous system;

said catheter body comprising a main axial portion and an angled distal end portion extending from said main axial portion, said second portion of said catheter body being disposed on said angled distal end portion of said catheter body;

said predetermined analyte having a specific relationship to an organ associated with said visceral venous system such that values of said analyte within said visceral venous system are substantially different from systemic values of said analyte outside said visceral venous system;

an integral operating unit, said integral operating unit comprising detector means, selectively connected to said first and second fiberoptic sensor means, for comparing said signals from said first and second fiberoptic sensor means and for alerting a user to a substantial difference between said signals;

third fiberoptic sensor means for monitoring the oxygen saturation of blood in said visceral venous system, said third fiberoptic sensor means being disposed substantially at a distal end of said catheter body;

means for measuring blood flow in said visceral venous system, said blood flow measuring means comprising said first and second fiberoptic sensor means; and said integral operating unit further comprising:

illuminating means for transmitting light to said first, second, and third fiberoptic sensor means;

a microprocessor;

program memory programmed for computing concentration values of said predetermined analyte and for storing at least one equation for calculating blood flow values based on said concentration values; and said microprocessor receives said signals from said first and second fiberoptic sensor means and utilizes said program memory to calculate concentration values of said predetermined analyte based on said signals from said first and second fiberoptic sensor means, and to calculate said blood flow values utilizing said at least one stored equation and said concentration values.

19. A multifunctional visceral catheter according to claim 18, wherein:

each of said first, second, and third fiberoptic sensor means comprises an optical fiber having an optode sensor provided at an analyte-detecting end of said optical fiber;

said optode sensor of said third fiberoptic sensor means comprises an oxygen optode.

20. A multifunctional visceral catheter according to claim 19, wherein:

said predetermined visceral venous system comprises the hepatic venous system;

said predetermined analyte comprises galactose;

each of said optode sensors of said first and second fiberoptic sensor means comprises biochemical sensor material provided within a semipermeable membrane; and said biochemical sensor material generates fluorescent signals which vary according to detected values of galactose.

* * * * *